United States Patent [19]

Danby

[11] Patent Number: 5,779,207

[45] Date of Patent: Jul. 14, 1998

[54] MEDICAL DEVICE CLAMP

[75] Inventor: Hal Danby, Sudbury, England

[73] Assignee: Baxter International, Inc., Deerfield, Ill.

[21] Appl. No.: 664,629

[22] Filed: Jun. 17, 1996

[30] Foreign Application Priority Data

Apr. 17, 1996 [GB] United Kingdom ............... 9607981

[51] Int. Cl.$^6$ ........................................... A47B 96/06
[52] U.S. Cl. .................................. 248/230.4; 248/218.4
[58] Field of Search ................. 248/230.4, 230.3, 248/229.13, 230.2, 230.1, 231.31, 231.51, 219.4, 218.4; 24/525, 569; 5/503.1, 658, 507.1

[56] References Cited

U.S. PATENT DOCUMENTS

| | | |
|---|---|---|
| 2,711,300 | 6/1955 | Nelson et al. . |
| 2,798,404 | 7/1957 | Schaefer et al. . |
| 3,536,299 | 10/1970 | McCloud et al. . |
| 3,706,437 | 12/1972 | Eberhardt ........................ 248/230 |
| 4,190,224 | 2/1980 | LeBlanc et al. .................. 248/229 |
| 4,616,524 | 10/1986 | Bidoia . |
| 4,674,722 | 6/1987 | Danby et al. .................... 248/231.3 |
| 4,729,535 | 3/1988 | Frazier et al. ................... 248/230 |
| 4,844,397 | 7/1989 | Skakoon et al. . |
| 5,169,106 | 12/1992 | Rasmussen ...................... 248/230 |
| 5,332,184 | 7/1994 | Davis .............................. 248/231.4 |
| 5,482,239 | 1/1996 | Smith . |

FOREIGN PATENT DOCUMENTS

| | | |
|---|---|---|
| 0 225 012 | 10/1987 | European Pat. Off. . |
| 977086 | 1/1965 | Germany . |
| 0755763 | 8/1956 | United Kingdom . |
| 879878 | 10/1961 | United Kingdom . |
| 999678 | 7/1965 | United Kingdom . |
| 1420092 | 1/1976 | United Kingdom . |

Primary Examiner—Ramon O. Ramirez
Assistant Examiner—Willie Berry, Jr.
Attorney, Agent, or Firm—Francis C. Kowalik

[57] ABSTRACT

A clamp for a medical device such as an infusion pump has a plurality of orientations adapted to grip either substantially vertical or horizontal gripped members and has an actuation knob with extensible arms wherein the arms are operative to provide greater available torque to remove the clamp than is available to apply the clamp.

20 Claims, 3 Drawing Sheets

MEDICAL DEVICE CLAMP

FIELD OF THE INVENTION

This invention relates to clamps and more specifically to pole clamps used with medical infusion pumps.

BACKGROUND OF THE INVENTION

Prior clamps comprise a knob or handwheel which serves to drive a threaded shaft against a pole so as to provide, in conjunction with a pole gripping anvil, a friction connection between the pole and the pump. Modifications of this basic idea have been to use scissors or a lever to multiply the force applied by the threaded shaft to the pole or gripped member so as to improve the mechanical qualities of the clamp.

Prior clamps, however, suffer from the same flaw. These clamps require an equal amount of force to be applied to remove the clamp as was required to affix the clamp to the gripped member. In a hospital setting, wherein orderlies and nurses share the responsibilities of placing and removing pumps, this flaw comes to the fore. For example, consider the situation where an orderly affixes a pump to a pole. At a time subsequent to this installation, another person, having less strength than the orderly, wishes to remove the pump. However, to satisfy himself that the pump was firmly affixed to the pole, the orderly applied a great deal of torque to the knob. Since torque equals force times distance, the person wishing to remove the pump must supply at least as much force to the knob as the orderly did when installing the pump. For a more lightly muscled person this task may prove to be daunting or impossible.

This difficulty, repeated over and over, has an effect on the efficiency of the staff as well as providing a source of additional wear on the equipment, as tools are commonly employed to loosen these clamps.

European patent 567946A2 and European patent 567946A3 to Beckton Dickinson Co. describe a pole clamp incorporated in a pump housing wherein the clamp arm is moveable to a storage position which is substantially flush with the outer surface of the pump housing.

U.S. Pat. No. 5,482,239 to Smith discloses an attachment device designed to connect an intravenous container support apparatus to various medical transport and patient care devices such as wheelchairs, hospital beds, transport carts for emergency room and outpatient use, and ambulance cots.

U.S. Pat. No. 5,158,528 to Davis et al discloses a latch number which is movably mounted on the base member and is adapted to releasably retain the peristaltic pump on the base member.

U.S. Pat. No. 4,706,368 to Beaumont W. Hospital discloses a set of clamps adapted to support an I.V. flow sensor on a pole.

WO patent 9217226, corresponding to U.S. Pat. No. 5,225,0027, to Sherwood Medical Company discloses a support device (10) including an elongate channel (14).

U.S. Pat. No. 5,319,816 to Ruehl discloses an I.V. stand which is removably mountable to a hospital bed.

U.S. Pat. No. 5,170,817 discloses a support device for a fluid delivery system.

None of these devices disclose or claim the advantages inherent in the instant invention as described in the specification and claims appended hereto.

SUMMARY OF THE INVENTION

It is a primary object of the instant invention to provide a clamp, wherein the clamp is preferentially easier to remove than engage.

It is another object of the instant invention to provide for a means for increasing the applied torque to the clamp preferentially during removal.

It is a further object of the instant invention to provide a clamp which, while able to engage a gripped element securely, is easily removable.

It is another object of the instant invention to provide a clamp which has a plurality of orientations.

It is another object of the instant invention to provide for a clamp adapted to releasably affix a medical device to a plurality of objects commonly found in a hospital area or the like.

These and other objects of the instant invention will become apparent in the detailed description of the preferred embodiment and claims appended hereto.

DETAILED DESCRIPTION OF THE PREFERRED EMBODIMENT

Figure 1:
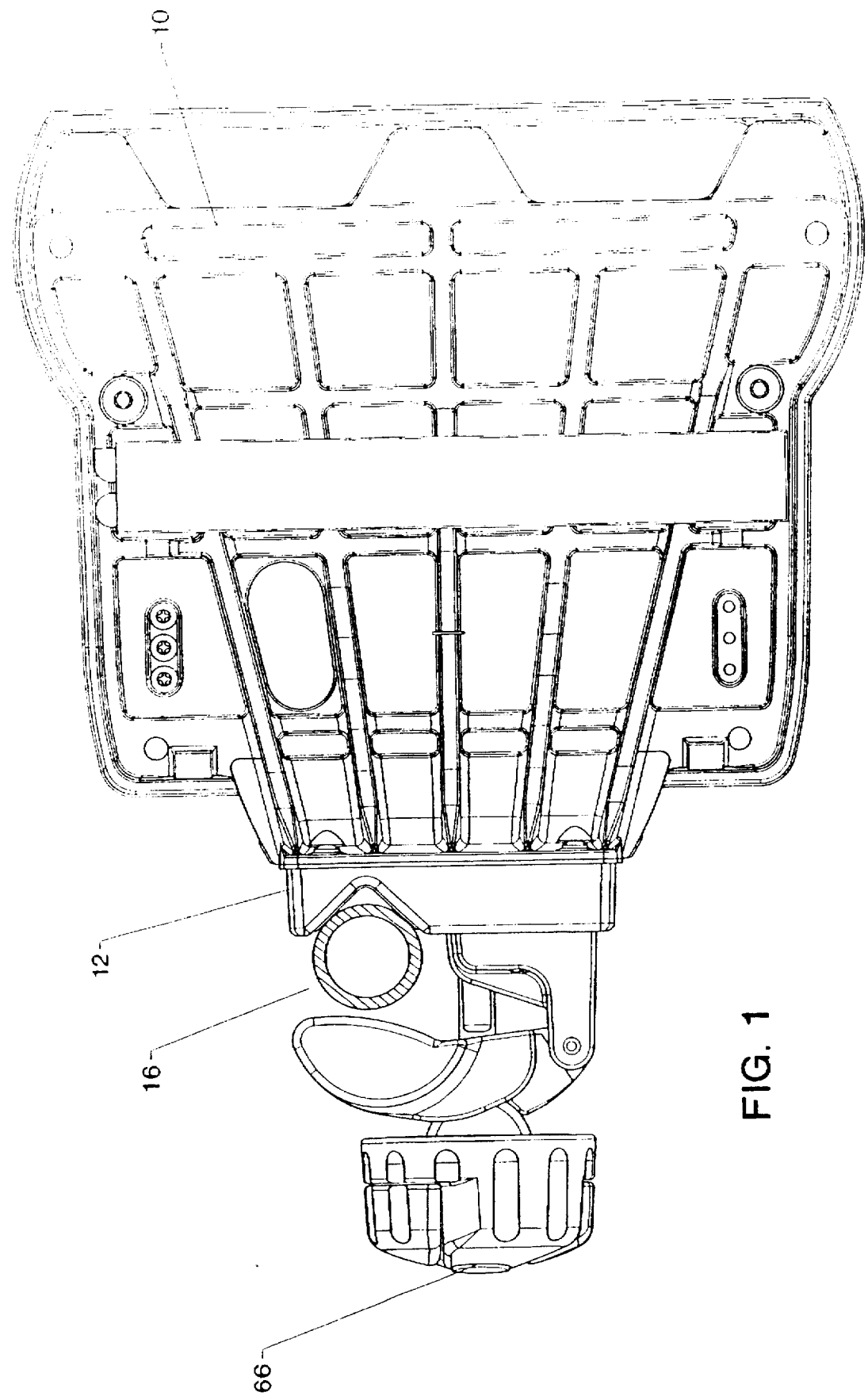
FIG. 1 is a plan view of the novel clamp.
Figure 2:
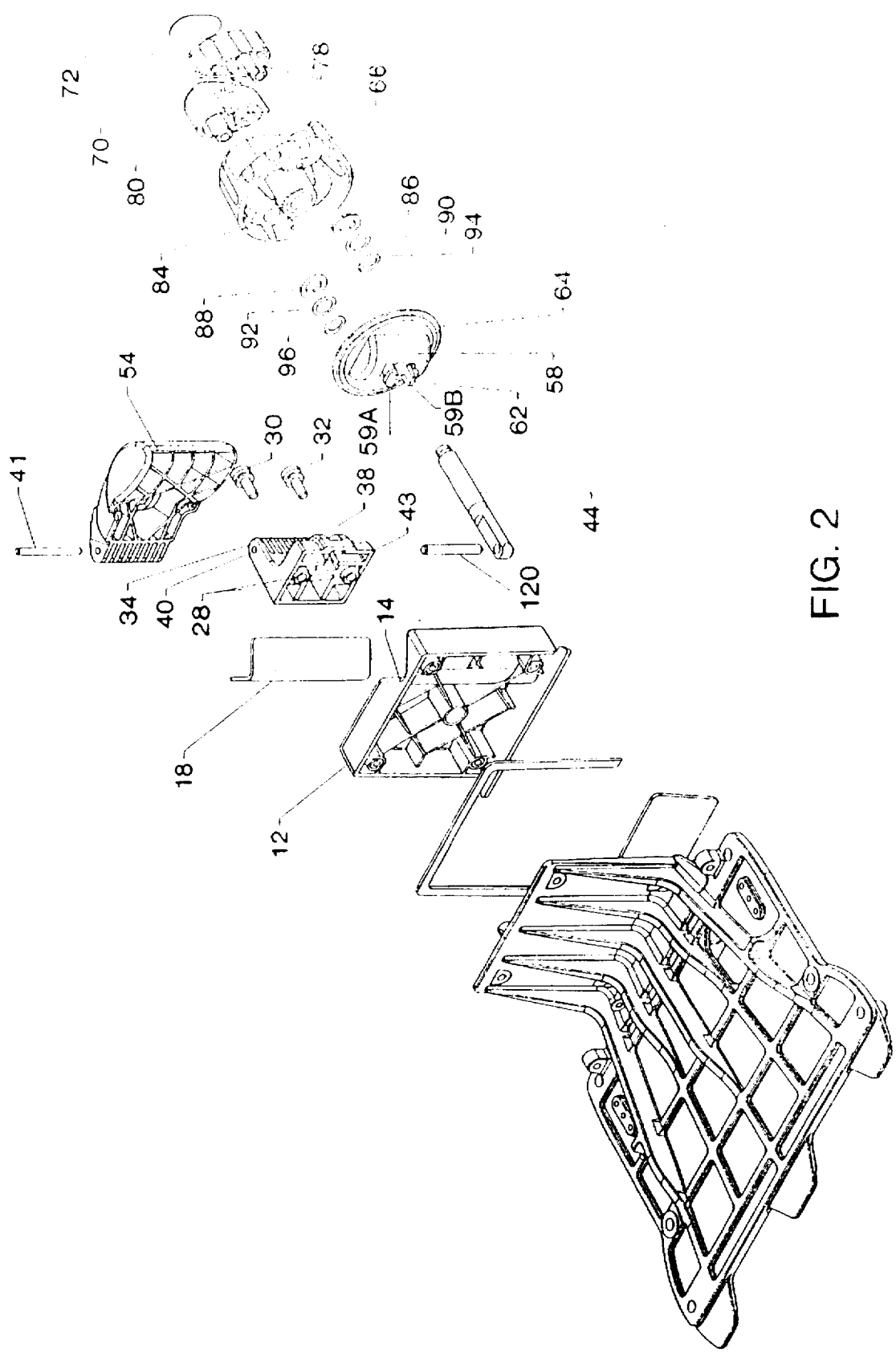
FIG. 2 is an exploded view of the novel clamp from the interior side thereof.
Figure 3:
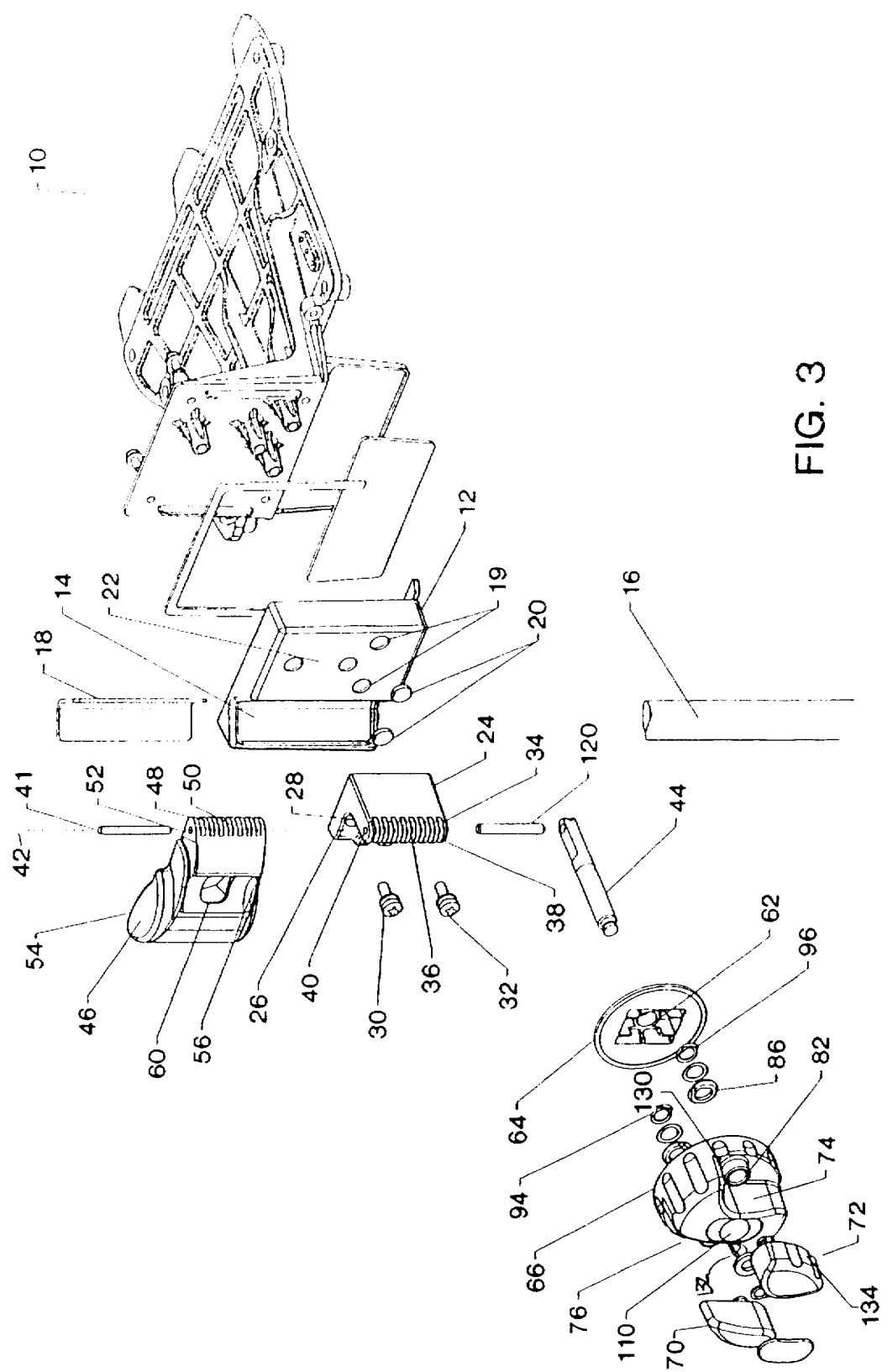
FIG. 3 is an exploded view of the novel clamp from the exterior side thereof.

Referring to FIG. 1, the preferred embodiment of the invention comprehends a baseplate 12 which is affixed to a device 10, wherein the baseplate 12 further comprehends a v-shaped groove 14. The groove is operative to partially surround a gripped member 16. The groove 14 further includes a friction enhancing insert 18, wherein the insert is conterminous with the groove 14. The baseplate 12 further defines a plurality of holes 19 therethrough operative to pass baseplate fasteners 20 through the baseplate 12 and into device 10 thereby affixing the baseplate thereto.

The baseplate 12 further defines a mounting surface 22 which mates with hinge plate 24. Hinge plate 24 comprises a body 26 which defines apertures 28 through which are passed mounting screws 30, 32 which serve to affix the hinge plate 24 to baseplate 12 or connect through baseplate 12 to device 10

Hinge plate body 26 further comprises a first hinge member 34 which has a plurality of tangs 36 which define first hinge member slots 38 thereby forming half of a piano type hinge. Tangs 36 further define a hinge pin apertures 40 which are transverse to the tangs 36, the center thereof defining a pivot axis 42 about which the hinge operates.

Hinge plate body 26 further provides an attachment point 43 for actuating shaft 44 and is thereby made a force carrying member.

Clamp member 46 comprehends a plurality of clamp member tangs 48 which are disposed to interdigitate with tangs 36 by means of the locating or clamp tangs slot 50 defined by the clamp tangs 48 as aforedescribed. Clamp tangs 48 further define tang apertures 52 which are disposed to align with hinge pin apertures 40 when the clamp tangs 48 are interdigitated with tangs 36 and are secured therewith by hinge pin 41.

Clamp body 46 further defines a curvilinear clamping surface 54 which is operative to securely urge gripped member 16 into V-shaped groove 14.

The body 46 further comprehends a hemicylindrical bearing surface 56 which allows the clamp body 46 to move thereabout while maintaining compressive force on the body 46 as actuated by threaded actuating shaft 44.

Nested in bearing surface 56 is slide member 58. Slide member 58 is co-operative with bearing surface 56 to provide a rotatable compressive coupling between shaft 44 and clamp body 46. The slide member 58 and the bearing surface both define apertures therethrough so as to allow threaded shaft 44 to pass through clamp body 46 and slide member 58. The clamp shaft aperture 60 is extended perpendicular to the clamp bodies rotation axis 42 so as to allow shaft 44 to pass freely therethrough. The slide member shaft aperture 62 is substantially co-extensive with threaded shaft 44, thereby acting to fix the shaft 44 in the slide member 58. bars 59A, 59B are operative with slide member 58 to attach slide member 58 to clamp body 46 for ease of manufacture.

Surmounting slide member 58, integral thrust plate 64 provides a smooth surface upon which rotary motion of associated elements may easily occur.

Outboard of thrust plate 64 activating knob 66 provides the primary activating means for the clamp member 46.

Associated with activating knob 66 are a plurality of torque arms 70, 72 which act co-operatively with arm indents 74, 76 in knob 66 to preferentially provide additional torque to decouple clamp member 46 from gripped article 16. Torque arms 70, 72 further comprehend arm shafts 78, 80 which pass through respective torque arm shaft apertures 82, 84 defined in knob 66. Arm shafts 78, 80 are formed non-cylindrical so as to engage respective frustro-conical thrust washers 86, 88 which are preloaded by wave washers 90, 92 so as to hold torque arms 70, 72 in a selected position. This aforementioned preloading is maintained by circlips 94, 96 which engage slots 98, 100 in torque arm shafts 78, 80.

In operation the clamp body 46 and groove 14 are placed about gripped element 16. When the relative location of the clamp 2 and gripped element 16 is that which is desired, knob 66 is rotated. The rotation of knob 66 causes threaded insert 110 to advance along threaded shaft 44 thereby applying a compressive force to slide member 58 and thereby closing clamp jaw 46 against gripped member 16. Threaded shaft 44 is prevented from rotating by clevis pin 120 inserted transversely therethrough in hinge plate body. Thrust plate 64, provides a low friction sliding surface which is operative to transfer compressive forces from the knob 66 to slide member 58. Furthermore, as base plate 12 has a plurality of alternative positions relative to device 10, the entire assembly can be rotatably adapted to grip either vertical or horizontal gripped members.

When it is desired for the clamp to be released, torque arms 70, 72 are extended from knob 66 to rest against knob stops 130, 132 so as to extend substantially radially outwardly from the circumferential periphery of the knob 66. An operator applies a force to the radially extended arms., thereby providing for increased torque to be applied to knob 66 so as to effect a release of the clamp 46 with reduced operator strain. Barbs 59A, 59B further serve to withdraw clamp member 46 from gripped member 16 during the release mode of operation.

It should be noted that the torque arms 70, 72 are radially coextensive with the circumferential periphery of the knob 66 when the knob is being actuated so as to close the clamp on gripped member 16. This is effected by arm pivots 78, 80, being located at one end of the arms wherein the arms themselves display a side 134 which is coextensive with the periphery of the knob when the arms are in a first position corresponding to the clamp being actuated. The arms further have a second position defined by their having greater radial extension than the circumferential periphery of the knob, when, as aforementioned, the clamp is being released.

In accordance with my invention I claim:

1. A clamp for removably affixing a device to a gripped element, said clamp comprising groove means, for partially encompassing said gripped element, clamp body means for releasably compressively urging said gripped element into contact with said groove means, and actuation means for releasably actuating said clamp body means wherein said actuation means includes torque means for preferentially allowing the application of more torque when said clamp body means is being released from said gripped element.

2. The invention, according to claim 1 and said actuation means, further comprising a knob for rotatively engaging a shaft wherein said combination is operative to actuate said clamp body means.

3. The invention according to claim 2 and said torque means further comprising at least one extensible arm means for introducing additional torque to said actuation means and, wherein said knob has an axis of rotation, said arm means being perpendicularly extensible from said axis.

4. The invention according to claim 3 and said extensible arm means having at least one arm, said arm having an axis of rotation of about a first end thereof, wherein said arm have a first end and a rotation about said axis serving to deploy said arm, and an inverse rotation serving to retract said arm.

5. The invention according to claim 4 and said arm, cooperative with said knob further comprising a first arm position and a second arm position.

6. The invention according to claim 5 and said first arm position comprising wherein said knob has a radial extension from said axis of rotation, said arm being substantially radially coextensive with said knob.

7. The invention according to claim 6 and a second arm position comprising said arm having a greater radial extension from said axis of rotation than the radial extension of said knob.

8. The invention according to claim 7 and said second arm position being operative to apply torque to said knob when force is applied to said arms to release said clamp.

9. The invention according to claim 8 and said arm being inoperative to apply torque to said knob when force is being applied to engage said clamp.

10. The invention according to claim 1, wherein said clamp means is orientable with respect to said device.

11. The invention according to claim 10 and said orientability having two states to grip vertical and horizontal gripped members.

12. A clamp for an infusion device comprising a baseplate having a plurality of mounting orientations wherein said orientations are adapted to effect releasable attachment of a device to at least one of a plurality of gripped elements, a jaw, operative in cooperation with said baseplate, to clamp releasably said gripped element and, an activating knob having at least one arm extensible therefrom, said arm operative to apply additional torque to said knob during a release of said clamp.

13. The invention according to claim 12 and said arm having a plurality of positions wherein said arm is coextensive with said knob when said gripped element is being clamped.

14. The invention according to claim 13 and said plurality of positions further comprising a position wherein said arm is extended radially outwardly from said knob when said clamp is being released from said gripped element.

15. The invention according to claim 12 and said knob further including stop means for restricting radial extension of said arm past a point of maximum radial extension.

16. The invention according to claim 12 and said jaw further comprising a curvilinear surface adapted to grip a gripped element wherein said gripped element is a pole.

17. The invention according to claim 16 and said curvilinear surface further adapted to grip a planar gripped member.

18. The invention according to claim 17 wherein said planar gripped member is a part of a hospital bed.

19. A method for attaching a medical device to a gripped member to as to releasably affix said device to said member comprising the steps of:

1. wherein said medical device has associated therewith a clamp adapted to partially encircle said gripped member, placing said clamp about said gripped member; and 2. wherein said clamp has associated therewith a means for actuating said clamp so as to apply a substantially compressive force to said gripped member as defined by said clamp, actuating said means for actuating said clamp; and 3. wherein said means for actuating said clamp is a rotatable knob, effecting such actuation by rotating said knob; and 4. wherein said knob has associated therewith at least one arm, extensible therefrom and operative to be extensible when said clamp is desired to be removed, extending said arm; and 5. wherein said arm is operative to exert torque to said knob to a greater extent than available to cause said knob to actuate said clamp to grip said gripped member, applying said torque by means of said arm; and 6. by means of said additional torque being made available to cause removal of said clamp from said gripped member, effecting removal of said clamp.

20. The method according to claim 19 and the additional prefatory step of orienting said clamp to adapt to the orientation of said gripped member wherein said gripped member has an orientation.

* * * * *